United States Patent [19]

Seltzer et al.

[11] 4,071,477
[45] Jan. 31, 1978

[54] HYDANTOIN DIGLYCIDYL COMPOUNDS

[75] Inventors: Raymond Seltzer, New City; David A. Gordon, Scarsdale, both of N.Y.

[73] Assignee: Ciba-Geigy Corporation, Ardsley, N.Y.

[21] Appl. No.: 694,741

[22] Filed: June 10, 1976

[51] Int. Cl.² .................... C08G 59/26; C07D 233/78
[52] U.S. Cl. .................... 260/2 N; 260/2 EP; 260/2 EC; 260/2 EA; 260/9; 260/28 R; 260/37 EP; 260/78.41; 260/836; 548/309
[58] Field of Search ............ 260/2 EP, 2 N, 309.5

[56] References Cited

U.S. PATENT DOCUMENTS

| | | | |
|---|---|---|---|
| 3,449,353 | 6/1969 | Porret et al. | 260/309.5 |
| 3,809,660 | 5/1974 | Habermeier et al. | 260/2 EP |

*Primary Examiner*—Harold D. Anderson
*Assistant Examiner*—E. A. Nielsen

*Attorney, Agent, or Firm*—Vincent J. Cavalieri

[57] ABSTRACT

Hydantoin diglycidyl compounds of the formula

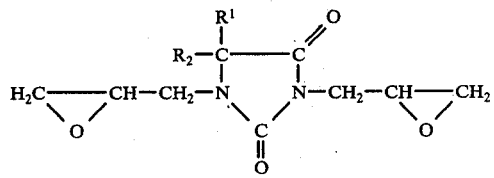

wherein $R_1$ is hydrogen, alkyl containing 1 to 8 carbon atoms or cycloalkyl containing 5 to 6 carbon atoms; and $R_2$ is alkyl containing 5 to 8 carbon atoms or cycloalkyl containing 5 to 6 carbon atoms, are prepared. The diglycidyl compounds are liquid at room temperature, easily processable as casting and laminating resins and when cured possess excellent resistance to water.

10 Claims, No Drawings

HYDANTOIN DIGLYCIDYL COMPOUNDS

DETAILED DESCRIPTION

This invention relates to novel hydantoin diglycidyl resins of the formula

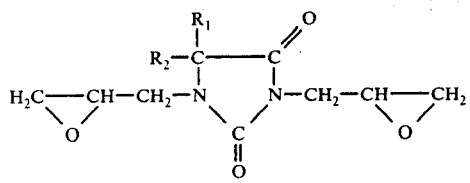 (I)

wherein $R_1$ is hydrogen, alkyl containing 1 to 8 carbon atoms or cycloalkyl containing 5 to 6 carbon atoms; and $R_2$ is alkyl containing 5 to 8 carbon atoms or cycloalkyl containing 5 to 6 carbon atoms.

The alkyl group employed herein includes both straight- and branched-chain alkyl groups, examples of which are methyl, ethyl, propyl, isopropyl, butyl, pentyl, neopentyl, amyl, sec-amyl, isoamyl, hexyl, octyl, and the like. The cycloalkyl groups include cyclopentyl and cyclohexyl.

Preferably, $R_1$ is hydrogen, or alkyl containing 1 to 8 carbon atoms; and $R_2$ is alkyl containing 5 to 8 carbon atoms.

Most preferably, $R_1$ is H, or alkyl containing 1 to 6 carbon atoms and $R_2$ is alkyl containing 5 to 6 carbon atoms.

Prior art hydantoin diglycidyl resins are disclosed in U.S. Pat. No. 3,489,353, which have the formula

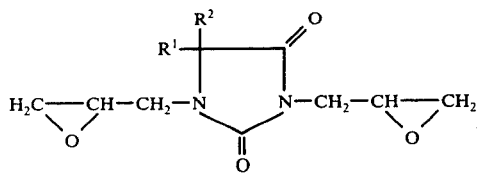

in which $R_1$ and $R_2$ each denote a hydrogen atom or an aliphatic or cycloaliphatic hydrocarbon residue, preferably a lower alkyl residue having 1 to 4 carbon atoms, or in which $R_1$ and $R_2$ jointly form a bivalent aliphatic or cycloaliphatic hydrocarbon residue, preferably a tetramethylene or pentamethylene residue.

The hydantoin diglycidyl resins of this patent, however, when used as a room temperature cured casting or laminating resin, for example, in the electrical, building and decorative areas, have the disadvantage of being crystalline solids or being highly viscous and the "lower alkyl" examples display poor resistance to water. Thus, the mechaical and electrical properties for these cured products rapidly disintegrate on continual exposure to water or humidity, rendering them of little value in these applications.

The diglycidyl hydantoin resins of this invention having an alkyl group of 5 to 8 carbon atoms in the 5 position of the hydantoin ring have significant advantages over the "lower alkyl" examples described in the aforementioned patent. The compounds of this invention have generally lower viscosity which results in easier processing and are especially suitable as a casting and laminating resin. The cured compounds have lower dielectric constants which results in improved electrical properties and, of most significance, the cured compounds have greater water resistance, especially when cured with amines at room temperature.

The intermediate hydantoins of the formula

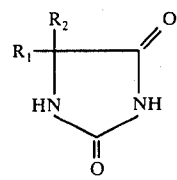

can be prepared by the well-known method of using a given ketone, sodium cyanide and ammonium carbonate. The resins of this invention can then be prepared in the usual way using epichlorohydrin, tetramethylammonium chloride (TMAC) and alkali, e.g.,

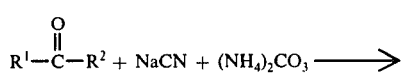

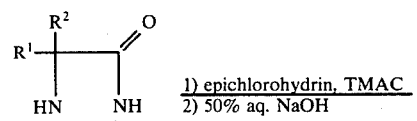

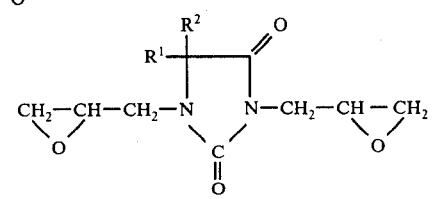

The diglycidyl hydantoin resins of this invention are especially suitable for use as room temperature cured casting and laminating resins. The curable epoxide may be employed in the fields of surface protection, the electrical industry, laminating processes and the building industry. More specifically, the diglycidyl hydantoin resins of this invention when combined with the appropriate curing agents may be used as insulating compositions for electrical parts, as compositions to prepare printed circuit boards and can coatings, and further, as compositions for the preparation of structural laminates and flooring.

The diglycidyl hydantoin resins according to this invention react with the customary acid and basic type curing agents for epoxide compounds for both room temperature and heat curing systems. However, in their preferred use as a casting and laminating resin, the basic room temperature type curing agents are especially preferred.

As suitable room temperature type basic curing agents there may, for example, be mentioned amines such as aliphatic, cycloaliphatic or heterocyclic, primary, and secondary amines, e.g. aliphatic polyamines such as diethylenetriamine, triethylenetetramine, N-(2-hydroxyethyl)-, N-(2-hydroxypropyl)- and N-(2-cyanoethyl)-diethylenetriamine, tetraethylenepentamine, propane-1,2-di-amine, propane-1,3-diamine, and 2,2,4- and 2,3,3-trimethyhexane-1,6-diamines, ethylenediamine, hexamethylenediamine, trimethyhexamethylenediamine, N,N-dimethylpropylenediamine-1,3, N,N-diethypropylenediamine-1,3; cycloaliphatic polyamines such as bis(4-aminocyclohexyl)methane, bis(4-amino-3-methylcyclohexyl)methane, 2,2-bis(4-aminocyclohexyl)propane and 3-aminomethyl-3,5,5-trimethylcyclohexylamine (isophoronediamine); and heterocyclic polyamines such as N-(2-aminoethyl)-piperazine.

Although not preferred, acid and basic type curing agents, which require some heating, may also be used to cure the hydantoin diglycidyl compounds of this invention, e.g., polycarboxylic acid anhydrides such as phthalic anhydride, 1,2,3,6-tetrahydrophthalic anhydride, methyl-1,2,3,6-tetrahydrophthalic anhydride, methyldomethylene-1,2,3,6-tetrahydrophthalic anhydride, hexahydrophthalic anhydride, benzophenone-3,3',4-4'-tetracarboxylic acid dianhydride, pyromellitic dianhydride, maleic anhydride, succinic anhydride, dodecenylsuccinic anhydride, nonenylsuccinic anhydride, polysebacic anhydride and polyazelaic anhydride, as well as polycarboxylic acids such as phthalic acid, 1,2,3,6-tetrahydrophthalic acid, hexahydrophthalic acid, isophthalic acid, terephthalic acid, adipic acid, succinic acid, dodecenylsuccinic acid, maleic acid, citric acid, mellitic acid and pyromellitic acid; and polyhydric phenols such as resorcinol, hydroquinone, 2,2-bis(4-hydroxyphenyl)propane and resins formed between formaldehyde and phenols such as phenol itself or p-chlorophenol. Aromatic amines such as, aromatic polyamines such as bis-(4-aminophenyl)methane, bis(4-aminophenyl)sulphone, and p- and m-phenylenediamines, and m-xylylenediamine; and dicyandiamide.

There may also be used catalytic curing agents, including aliphatic, cycloaliphatic, heterocyclic or aromatic tertiary amines such as 2,4,6-tris(dimethylaminomethyl)phenol, n-benzyldimethylamine, triethanolamine; alkali metal alkoxides of alcohols such as 2,4-dihydroxy3-hydroxymethylpentane; stannous salts of alkanoic acids, such as stannous octoate; and Lewis Acid catalysts such as boron trifluoride and its complexes.

The acid-type curing agents such as polycarboxylic acid anhydrides, are normally used in a proportion such as to supply from 0.7 to 1.2 carboxylic acid anhydride equivalents per 1,2-epoxide group of the polyepoxide; the preferred polyamines which are normally used in a proportion such as to supply from 0.8 to 1.2 amino-hydrogen equivalents per 1,2-epoxide group of the diepoxide; and tertiary amine curing agents, present in quantity sufficient to convert the polyepoxide into an infusible, insoluble product.

The diglycidyl resins according to the invention or their mixtures with other polyepoxide compounds and/or curing agents can be mixed, before curing, with customary modifiers, such as extenders, fillers and reinforcing agents, pigments, dyestuffs, plasticisers, flow control agents, agents for conferring thixotropy, flame-proofing substances and mold release agents.

As extenders, reinforcing agents, fillers and pigments which can be introduced into the curable mixtures according to the invention there may, for example, be mentioned: coal tar, bitumen, glass fibres, boron fibres, carbon fibres, cellulose, polyethylene powder, slate powder, aluminum oxide trihydrate, chalk powder, gypsum, antimony trioxide, bentones, silica aerogel, (AEROSIL), lithopone, baryte, titanium dioxide, carbon black, graphite, iron oxide or metal powders, such as aluminum powder or iron powder.

To further illustrate the nature of this invention and the processes employed in preparing and curing the diglycidyl hydantoin resins of this invention, the following examples are given below:

A. PREPARATION OF HYDANTOINS

5-sec-Amyl-5-Ethylhydantoin

To a slurry of ammonium carbonate (865 parts), sodium cyanide (180 parts) in water (1200 parts) was added 5-methyl-3-heptanone (385 parts) in ethanol (1200 parts) at ambient temperature with stirring. The reaction mixture was heated to 55° C over a period thirty minutes and maintained at 55° C for 6 hours. After cooling to ambient temperature, chloroform (1000 parts) was added and the mixture stirred for ten minutes. The reaction mixture was filtered and the filter cake washed with additional chloroform (500 parts). The organic phase was collected and the aqueous phase washed with additional chloroform (1000 parts) in two portions. The combined organic phase was evaporated to dryness yielding crude product. The resultant white solid was slurried in water (2000 parts), filtered and dried to constant weight to afford 5-sec-amyl-5-ethylhydantoin (560 parts, 94% yield; mp 151°-6° C.

Cal'c. C, 60.58; H, 9.15; N, 14.13. Found C, 60.54; H, 9.44; N, 14.04.

The following hydantoin were prepared employing the above procedure:
5-n-Amyl-5-methylhydantoin (Mp 101°-3° C, 94%)
5-i-Amyl-5-methylhydantoin (Mp 158°-161° C, 90%)
5-n-Hexyl-5-methylhydantoin (Mp 107°-110° C, 96%)
In a similar manner, by substituting the appropriate ketone or aldehyde for the 5-methyl-3-heptanone in the above example, the following hydantoin compounds are obtained:
5-amylhydantoin
5-hexyl-5-ethylhydantoin
5-octylhydantoin
5-cyclohexyl-5-methylhydantoin
5-heptyl-5-methylhydantoin
5-octyl-5-amylhydantoin
5,5-dicyclohexylhydantoin
5,5-dioctylhydantoin

B. PREPARATION OF HYDANTOIN GLYCIDYL RESINS

1,3-Diglycidyl-5-sec-Amyl-5-Ethylhydantoin

A mixture of 5-sec-amyl-5-ethylhydantoin (397 parts), epichlorohydrin (1575 parts) and tetramethylammonium chloride (10 parts) was heated slowly to 80° C over a period of one hour and maintained at 80° C for 2.5 hours. The reaction mixture was cooled to 60° C and a reflux was established by reducing pressure. Fifty percent aqueous sodium hydroxide (416 parts) was added dropwise over 2.5 hours while water was removed azeotropically by a circulatory distillation. The reaction mixture was cooled to 40° C, filtered and the filter cake washed with additional epichlorohydrin (500 parts). The filtrate was treated with activated charcoal (2 parts) and filtered through a pad of filter aid. The filtrate was concentrated to near dryness to yield the crude resin. The resin was diluted with chloroform (2000 parts) and washed with water (1000 parts). The organic phase was dried with magnesium sulfate (250 parts), filtered and concentrated to dryness to afford 584 parts (94% yield) of 1,3-diglycidyl-5-sec-amyl-5-ethylhydantoin as a pale yellow resin; epoxy value of 6.18 eq/kg (96% of theory), Cl, 0.75%.

The following resins were also prepared following the above procedure.

| Resin | Yield | Epoxy Value eq/Kg | %Cl |
|---|---|---|---|
| 1,3-Diglycidyl-5-Amyl-5-Methylhydantoin | 100% | 6.70 (99%) | 0.80 |
| 1,3-Diglycidyl-5-i-Amyl-5-Methylhydantoin | 93% | 6.51 (97%) | 0.65 |
| 1,3-Diglycidyl-5-n-Hexyl-5-Methylhydantoin | 90% | 6.33 (98%) | 0.61 |

In a similar manner, by substituting the appropriate hydantoin for the 5-sec-amyl-5-ethylhydantoin in the above example, the following diglycidyl hydantoin compounds are obtained:
1,3-Diglycidyl-5-amylhydantoin
1,3-Diglycidyl-5-hexyl-5-ethylhydantoin
1,3-Diglycidyl-5-octylhydantoin
1,3-Diglycidyl-5-heptyl-5-methylhydantoin
1,3-Diglycidyl-5-octyl-5-amylhydantoin
1,3-Diglycidyl-5,5-di-n-octylhydantoin
1,3-Diglycidyl-5-cyclohexyl-5-methylhydantoin
1,3-Diglycidyl-5,5-dicyclohexylhydantoin

C. CURING EXAMPLES

EXAMPLE 1

To 120 parts of N,N'-diglycidyl-5-sec-amyl-5-ethyl-hydantoin, having an epoxide content of 6.22 eq/Kg and previously degassed under vacuum, was added 19.7 parts of triethylenetetramine (TETA). The mixture was stirred and degassed, and kept at room temperature by means of an ice bath. The casting composition was poured into a 6 inch × 6 inch × ⅛ mold and cured at room temperature for 14 days.

The cured molding had the following mechanical properties:
Flexural Strength: 11.2 Kpsi
Flexural Modulus: 436 Kpsi
Tensile Strength: 7.0 Kpsi
Tensile Modulus: 410 Kpsi The above composition cured at room temperature for 7 days followed by a 6 hour postcure at 100° C had the following mechanical properties:
Flexural Strength: 12.9 Kpsi
Flexural Modulus: 363 Kpsi
Tensile Strength: 10.0 Kpsi
Tensile Modulus: 343 Kpsi

EXAMPLE 2

To 100 parts of the resin described in Example 1 was added 37.3 parts of 4,4'-methylene-bis-(2-methylcyclohexylamine) (known commercially as Laromin C260). The casting composition was processed as described in Example 1. After 2 weeks at room temperature, a hard molding was obtained.

EXAMPLE 3

To the resin of Example 1 was added a stoichiometric amount of 2,4,4-trimethylhexamethylenediamine. The homogeneous mixture was cured as described in Example 1. The resulting molding has a flexural modulus of 425 Kpsi.

EXAMPLE 4

With 1,3-Diaminomethylcyclohexane

To the resin of Example 1 is added a stoichiometric quantity of 1,3-diaminomethylcyclohexane, and then cured as described to give a hard molding.

EXAMPLE 5

A mixture of 61.6 parts of 4,4'-methylenedianiline and 200 parts of the resin in Example 1 was heated to 65° C over a 15 minute period to give a homogeneous mixture. The mixture was stirred under vacuum for 15 minutes while cooling to 55° C. The casting composition was then poured into prewarmed 5 × 7 × ¼ inch and 6 × 7 × ⅛ inch molding and cured at 120° C for 24 hours followed by 4 hours at 175° C. After cooling to room temperature, the cured molding had the following properties:
Flexural Modulus: 353 Kpsi
Flexural Strength: 13.0 Kpsi
Tensile Modulus: 353 Kpsi
Tensile Strength: 10.9 Kpsi
HDT: 149° C

EXAMPLE 6

A mixture of 165 parts of the resin of Example 1 and 174 parts of hexahydrophthalic anhydride was warmed to 40°-48° C under vacuum for 15 minutes; 3.3 parts of benzyldimethylamine was added and degassing was continued for 5 minutes. The casting composition was poured into prewarmed 5 × 7 × ¼ inch and 6 × 7 × ⅛ inch molds and heated at 80° C for 3 hours followed by 2 hours at 150° C.

The cured castings had the following mechanical properties:
Flexural Strength: 15.8 Kpsi
Flexural Modulus: 397 Kpsi
Tensile Strength: 8.3 Kpsi
Tensile Modulus: 334 Kpsi

EXAMPLE 7

To 1,3-diglycidyl-5-i-amyl-5-methylhydantoin, having an epoxide equivalent of 6.52 eq/Kg, was added a stoichiometric quantity of triethylenetetramine. The mixture was processed and cured as described in Example 1 to give a hard molding with a flexural modulus of 466 Kpsi.

EXAMPLE 8

A mixture of 100 parts of the resin of Example 7 and 91.8 parts of hexahydrophthalic anhydride was treated as described in Example 6, but cured at 100° C for 18 hours followed by 4 hours at 100° C.

The cured casting had the following mechanical properties:
Flexural Modulus: 420 Kpsi
Flexural Strength: 13.9 Kpsi
Tensile Modulus: 339 Kpsi
Tensile Strength: 9.8 Kpsi

EXAMPLE 9

To 1,3-diglycidyl-5-n-hexyl-5-methylhydantoin, having an epoxide equivalent of 6.33 eq/Kg., was added a stoichiometric quantity of triethylenetetramine. The mixture was processed and cured as described in Example 1 to give a hard molding with a flexural modulus of 382 Kpsi.

EXAMPLE 10

The resin of Example 9 was cured with 97.6 phr of hexahydrophthalic anhydride as described in Example 6 to give a molding with the following mechanical properties:

Flexural Modulus: 371 Kpsi
Flexural Strength: 14.6 Kpsi
Tensile Modulus: 333 Kpsi
Tensile Strength: 10.9 Kpsi The following comparisons demonstrate the superior properties for the hydantoin diglycidyl compounds of this invention as compared to the compounds disclosed in U.S. Pat. No. 3,449,353.

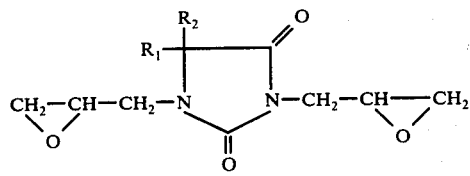

A. VISCOSITY COMPARISONS

With one exception the hydantoin glycidyl resins of this invention are lower in viscosity than the resins disclosed in U.S. Pat. No. 3,449,353.

|  | $R_1$ | $R_2$ | Gardener Viscosity 25° C |
|---|---|---|---|
| Compounds disclosed in U.S. 3,449,353 | $CH_3$ | $CH_3$ | 2900 cks crystallizes on standing |
|  | $CH_3$ | $C_2H_5$ | 1500–2000 cks |
|  | H | $C_3H_7$ | 3300 cks |
|  | $CH_3$ | n-$C_5H_{11}$ | 627 cks |
|  | $CH_3$ | i-$C_5H_{11}$ | 2000 cks |
| Compounds of the invention | $C_2H_5$ | sec-$C_5H_{11}$ | 627–1000 cks |
|  | $CH_3$ | n-$C_6H_{13}$ | 600 cks |

B. DIELECTRIC PROPERTIES (ASTM D150-70)

1. Hexahydrophthalic Anhydride Cured Castings

The curing agent and glycidyl compounds were mixed in equivalent ratios of 0.9–1.1 and cured as described. The samples were cured at 80°–100° C for 3–18 hours followed by 2–4 hours at 100° C. It was found by Torsional Brand analyses, and mechanical testing that the indicated cure conditions and mole ratios gave optimum properties.

|  | H/R | Cure | Preheat | $R^1$ | $R^2$ | Dielectric Constant (1000 hz) |
|---|---|---|---|---|---|---|
|  | 0.9 | 80/16 + 150/2 | 80/0.4 | $CH_3$ | $CH_3$ | 3.30 |
| Compounds disclosed in U.S. 3,449,353 | 0.94 | 80/16 + 150/2 | 50/0.17 | $CH_3$ | $C_2H_5$ | 3.37 |
|  | 1.1 | 80/5 + 150/2 | 45/0.92 | H | n-$C_3H_7$ | 3.33 |
|  | 0.9 | 100/18 + 150/4 | — | $CH_3$ | n-$C_5H_{11}$ | 2.98 |
| Compounds of the invention | 0.9 | 80/16 + 150/2 | 50/0.17 | $CH_3$ | i-$C_5H_{11}$ | 3.23 |
|  | 1.1 | 80/3 + 150/2 | 40/0.75 | $C_2H_5$ | sec-$C_5H_{11}$ | 3.13 |
|  | 1.0 | 80/3 + 150/2 | — | $CH_3$ | n-$C_6H_{13}$ | 2.87 |

2. Triethylenetetramine (TETA) Cured Castings

The curing agent and diglycidyl compounds were mixed in a stoichiometric amount. The samples were cured at room temperature (25° C) for two weeks.

|  | $R^1$ | $R^2$ | Dielectric Constant (1000 Hz) |
|---|---|---|---|
|  | $CH_3$ | $CH_3$ | 4.00 |
| Compounds disclosed in U.S. 3,449,353 | $CH_3$ | $C_2H_5$ | 3.90 |
|  | H | n-$C_3H_7$ | 3.90 |
| Compounds of the invention | $C_2H_5$ | sec-$C_5H_{11}$ | 3.44 |
|  | $CH_3$ | n-$C_6H_{13}$ | 3.48 |

C. EFFECT OF WATER ON TETA CURED HYDANTOIN RESINS

The resin and curing agent were mixed in stoichiometric amounts and cured at room temperature (25° C) for two weeks in molds ⅛ inch thick as described in Example 1. When cured, the sheets were cut into test pieces 1 × 3 × ⅛ inch and tested in flexure to a maximum outer-fiber strain of 0.5%.

TABLE I

1. Immersion in Distilled Water at Room Temperature (25° C)

|  | $R^1$ | $R^2$ | % Wt. Gain 24 Hrs | % Wt. Gain 1 Wk | % Wt. Gain 4 Wks | Init. Flex. Modulus/Kpsi | % Flex. Mod. Retained 24 Hrs | % Flex. Mod. Retained 1 Wk | % Flex. Mod. Retained 4 Wks |
|---|---|---|---|---|---|---|---|---|---|
| Compounds disclosed in U.S. Pat. No. 3,449,353 | $CH_3$ | $CH_3$ | 27.7 | Disintegrated |  | 668 | soft | Disintegrated |  |
|  | $CH_3$ | $C_2H_5$ | 13.4 | Disintegrated |  | 500 | 11 | Disintegrated |  |
|  | H | n-$C_3H_7$ | 14.5 | Disintegrated |  | 514 | 10 | Disintegrated |  |
| Compounds of the invention | $CH_3$ | i-$C_5H_{11}$ | 2.4 | 5.2 | 11.5 | 466 | 79 | 77 | 71 |
|  | $C_2H_5$ | sec-$C_5H_{11}$ | 1.4 | 2.6 | 5.8 | 466 | 81 | 78 | 71 |
|  | $CH_3$ | n-$C_6H_{13}$ | 1.4 | 3.6 | 6.8 | 382 | 72 | 77 | 79 |

TABLE II

|  | $R_1$ | $R_2$ | 2. Exposure to 95% Relative Humidity (35° C) | | | Init. Flex. Modulus/Kpsi | % Flex. Mod. Retained | | |
|---|---|---|---|---|---|---|---|---|---|
|  |  |  | % Wt. Gain | | | | | | |
|  |  |  | 24 Hrs | 1 Wk | 4 Wks |  | 24 Hrs | 1 Wk | 4 Wks |
| Compounds disclosed in U.S. Pat. No. 3,449,353 | $CH_3$ | $CH_3$ | 8.3 | 26.2 | Disintegrated | 652 | 28 | Disintegrated | |
|  | $CH_3$ | $C_2H_5$ | 4.9 | 13.5 | Disintegrated | 588 | 71 | 51 | Disintegrated |
|  | H | $n-C_3H_7$ | Sample tacky and broke on handling | Disintegrated | | 535 | Sample tacky and broke on handling | Disintegrated | |
| Compounds of the invention | $CH_3$ | $i-C_5H_{11}$ | 1.8 | 5.0 | 10.3 | 461 | 86 | 80 | 76 |
|  | $C_2H_5$ | $sec-C_5H_{11}$ | 1.0 | 2.7 | 4.9 | 467 | 84 | 80 | 75 |
|  | $CH_3$ | $n-C_6H_{11}$ | 1.5 | 3.9 | 7.1 | 391 | 79 | 81 | 64 |

What is claimed is:

1. A hydantoin diglycidyl compound of the formula

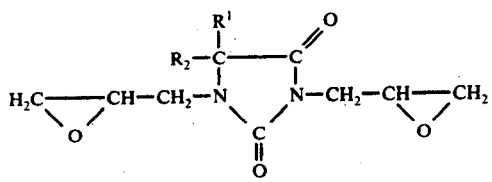

wherein $R_1$ is hydrogen, alkyl containing 1 to 8 carbon atoms or cycloalkyl containing 5 to 6 carbon atoms; and $R_2$ is alkyl containing 5 to 8 carbon atoms or cycloalkyl containing 5 to 6 carbon atoms.

2. The compound of claim 1 wherein $R_1$ is hydrogen or alkyl containing 1 to 8 carbon atoms and $R_2$ is alkyl containing 5 to 8 carbon atoms.

3. The compound of claim 2 wherein $R_1$ is methyl and $R_2$ is n-amyl.

4. The compound of claim 2 wherein $R_1$ is ethyl and $R_2$ is sec-amyl.

5. The compound of claim 2 wherein $R_1$ is methyl and $R_2$ is i-amyl.

6. The compound of claim 1 wherein $R_1$ is methyl and $R_2$ is n-hexyl.

7. The compound of claim 1 wherein $R_1$ is ethyl and $R_2$ is hexyl.

8. A curable composition comprising a diglycidyl hydantoin compound of claim 1 and a curing agent for epoxy resins.

9. The curable composition of claim 8 wherein said curing agent is a basic room temperature type curing agent.

10. The curable composition of claim 9 wherein said curing agent is an aliphatic polyamine.

* * * * *